United States Patent
Luo

(10) Patent No.: US 11,332,481 B2
(45) Date of Patent: May 17, 2022

(54) HOLE TRANSPORTING MATERIAL USING DIHYDROPHENAZINE AS CORE AND ORGANIC LIGHT EMITTING DIODE

(71) Applicant: WUHAN CHINA STAR OPTOELECTRONICS SEMICONDUCTOR DISPLAY TECHNOLOGY CO., LTD., Hubei (CN)

(72) Inventor: Jiajia Luo, Wuhan (CN)

(73) Assignee: WUHAN CHINA STAR OPTOELECTRONICS SEMICONDUCTOR DISPLAY TECHNOLOGY CO., LTD., Hubei (CN)

( * ) Notice: Subject to any disclaimer, the term of this patent is extended or adjusted under 35 U.S.C. 154(b) by 208 days.

(21) Appl. No.: 16/652,835

(22) PCT Filed: Feb. 14, 2020

(86) PCT No.: PCT/CN2020/075271
§ 371 (c)(1),
(2) Date: Apr. 1, 2020

(87) PCT Pub. No.: WO2021/098050
PCT Pub. Date: May 27, 2021

(65) Prior Publication Data
US 2022/0002316 A1     Jan. 6, 2022

(30) Foreign Application Priority Data
Nov. 22, 2019   (CN) .......................... 201911154297.6

(51) Int. Cl.
C07D 519/00   (2006.01)
H01L 51/00   (2006.01)
H01L 51/50   (2006.01)

(52) U.S. Cl.
CPC ........ *C07D 519/00* (2013.01); *H01L 51/0072* (2013.01); *H01L 51/5056* (2013.01)

(58) Field of Classification Search
CPC ............ H01L 51/0072; H01L 51/5056; C07D 519/00
See application file for complete search history.

(56) References Cited

U.S. PATENT DOCUMENTS

2020/0227655 A1*   7/2020   Ran ..................... H01L 51/0094

FOREIGN PATENT DOCUMENTS

CN           110183426 A   *   8/2019

OTHER PUBLICATIONS

Luo, J. CN 110183426 A Aug. 30, 2019, English machine translation, [database online], [retrieved on Jan. 1, 2022] Retrieved from Google Patents using Internet <URL: https://patents.google.com/patent/CN110183426A/en?oq=cn110183426> (Year: 2019).*

* cited by examiner

*Primary Examiner* — Amanda L. Aguirre

(57) ABSTRACT

A hole transporting material using dihydrophenazine as a core is disclosed, having a following structural formula (I) and suitable migration rates under highest occupied molecular orbital (HOMO) energy levels and lowest unoccupied molecular orbital (LUMO) energy levels. Moreover, an organic light emitting diode is disclosed, including an anode, a cathode, and a light emitting structure located between the anode and the cathode, wherein the light emitting structure includes the hole transporting material using dihydrophenazine as the core, which is represented by the following structural formula (I)

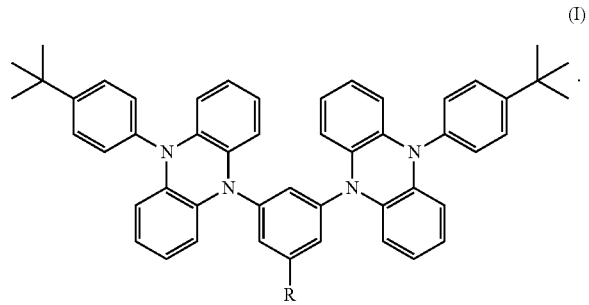

12 Claims, 1 Drawing Sheet

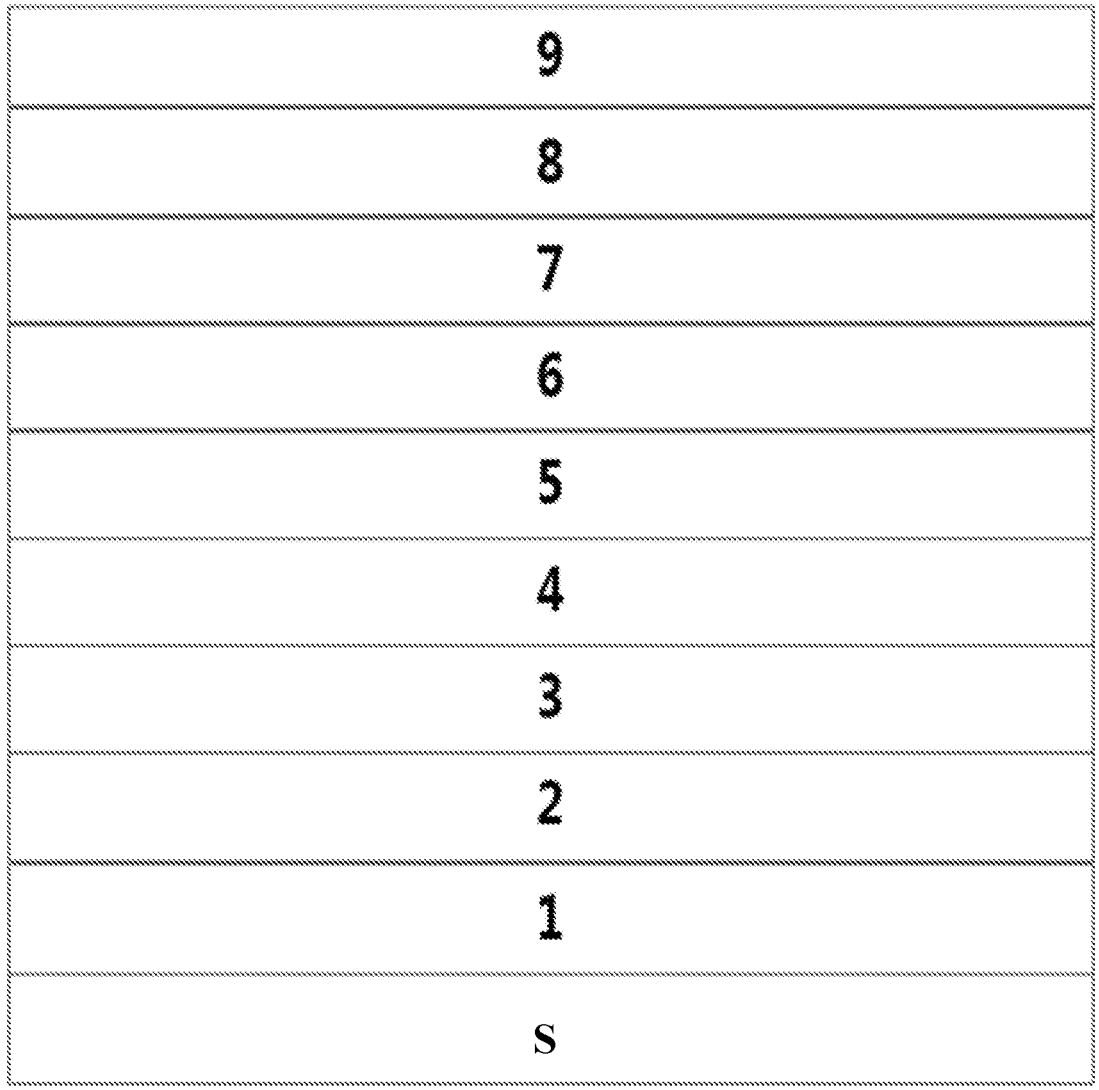

HOLE TRANSPORTING MATERIAL USING DIHYDROPHENAZINE AS CORE AND ORGANIC LIGHT EMITTING DIODE

FIELD OF INVENTION

The present invention relates to the technical field of organic light emitting material, and more particularly, to a hole transporting material using dihydrophenazine as a core and an organic light emitting diode fabricated by using the hole transporting material.

BACKGROUND

Organic light emitting diodes (OLEDs) have broad application prospects in fields of solid state lighting and flat panel displays, and light emitting materials are main factors affecting light emitting efficiency of organic light emitting diodes. In early days, light emitting guest materials used in organic light emitting diodes were fluorescent materials, having a ratio of singlet exciton and triplet excitons in an organic light emitting diode of 1:3. Therefore, in theory, an internal quantum efficiency (IQE) of the organic light emitting diode can only reach 25%, which limits application of fluorescent electroluminescent devices. Furthermore, due to spin-orbit coupling of heavy atoms, heavy metal complex phosphorescent materials can use both singlet and triplet excitons at a same time to achieve 100% internal quantum efficiency. However, in general, heavy metals used in the heavy metal complex phosphorescent light emitting materials are precious metals such as iridium (Ir) or platinum (Pt), and blue light materials of heavy metal complex phosphorescent light emitting materials still need to be improved.

For currently used top emitting organic light emitting diodes, hole transporting materials are used as a thickest layer, and its energy level and hole mobility have always been in contradiction. However, hole transporting materials with matching energy levels and high hole mobility are currently scarce. Therefore, it is necessary to provide a novel hole transporting material to solve the problems existing in the prior art.

SUMMARY

For currently used top emitting organic light emitting diodes, hole transporting materials with matching energy levels and high hole mobility are currently scarce. Therefore, it is necessary to provide a novel hole transporting material to solve the problems existing in the prior art.

In view of this, the present invention provides a hole transporting material using dihydrophenazine as a core, having the following structural formula (I):

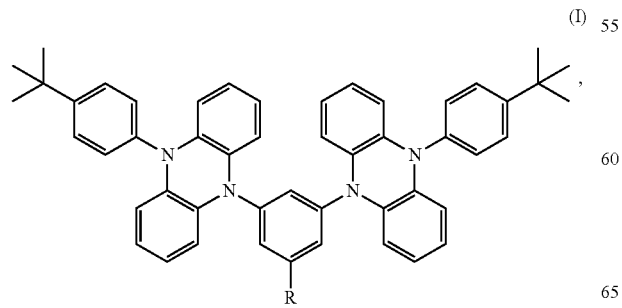

(I)

wherein R is

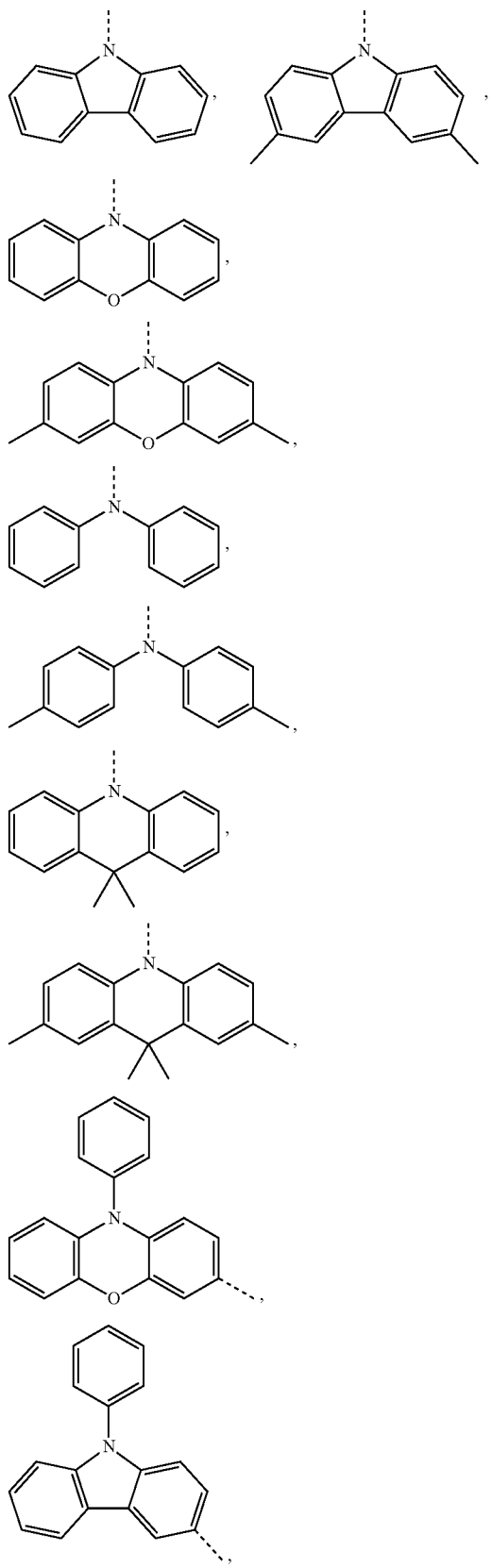

-continued

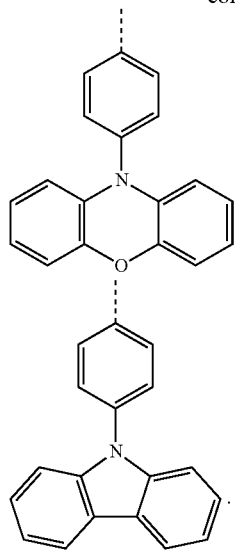

or

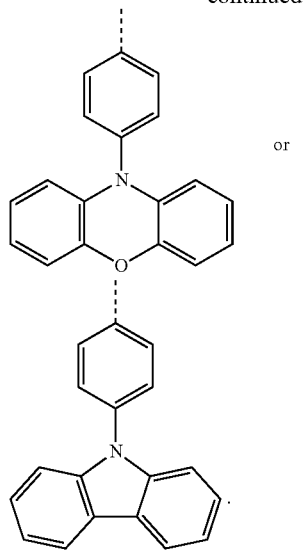

In one embodiment of the present invention, wherein the hole transporting material has the following structural formula:

In one embodiment of the present invention, wherein the hole transporting material is:

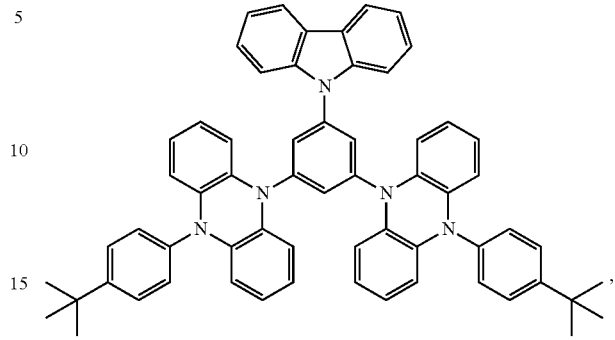

and is synthesized by the following synthesis route:

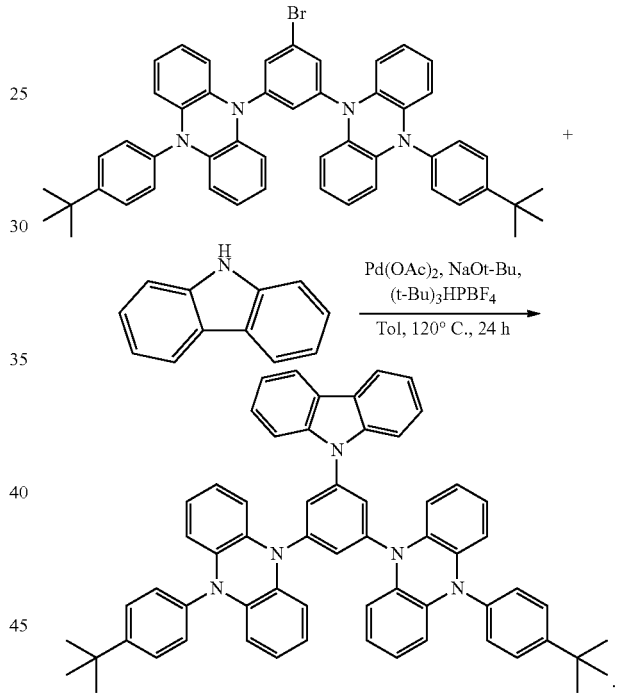

In another embodiment of the present invention, wherein the hole transporting material is:

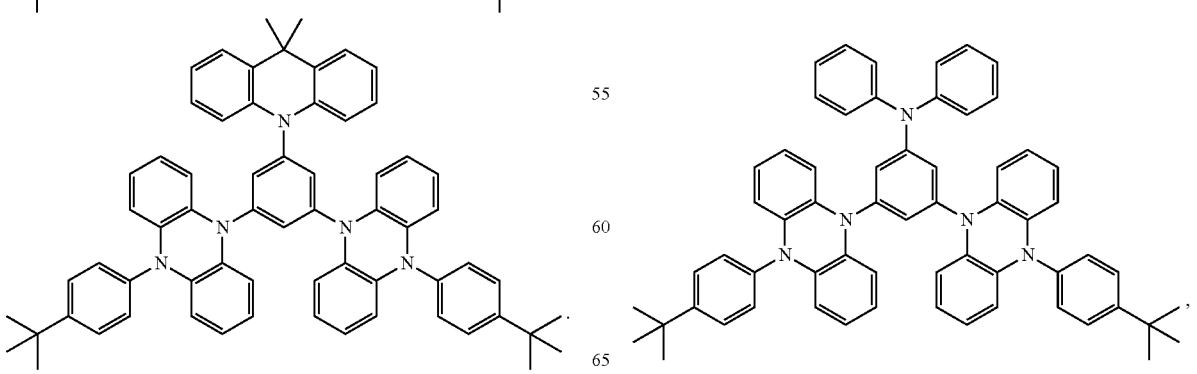

and is synthesized by the following synthesis route:

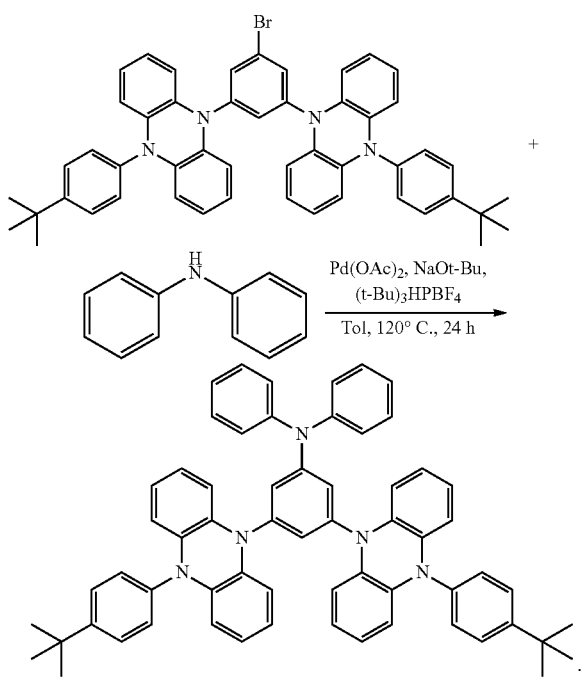

In yet another embodiment of the present invention, wherein the hole transporting material is:

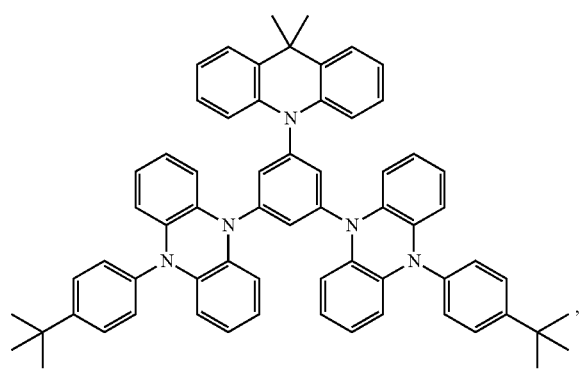 [SMILES: CC(C)(C)c1ccc(N2c3ccccc3N(c3cc(N4c5ccccc5N(c5ccc(C(C)(C)C)cc5)c5ccccc54)cc(N4c5ccccc5C(C)(C)c5ccccc54)c3)c3ccccc32)cc1]

and is synthesized by the following synthesis route:

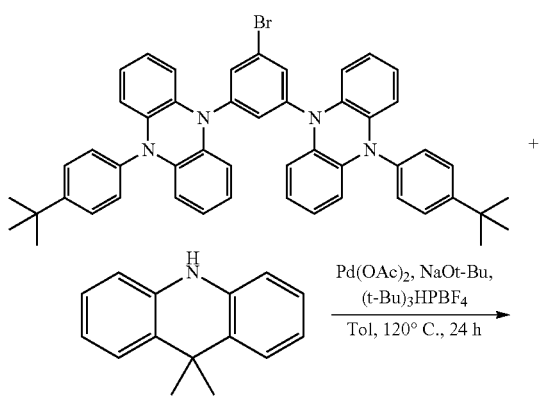

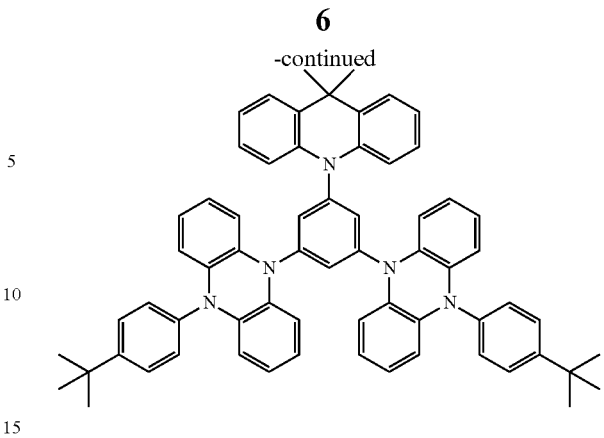

In another embodiment of the present invention, an organic light emitting diode is provided, wherein a material of a hole transporting layer in the organic light emitting diode is the hole transporting material using dihydrophenazine as a core described above.

The organic light emitting diode further comprises an anode, a cathode, and a light emitting structure located between the anode and the cathode, wherein the light emitting structure comprises the hole transporting material using dihydrophenazine as a core described above. The light emitting structure comprises a hole injecting layer, the hole transporting layer, an electron blocking layer, a light emitting layer, and a hole blocking layer, an electron transporting layer, and an electron injecting layer which are sequentially formed.

Compared with the prior art, hole transporting materials using dihydrophenazine as a core with suitable mobilities under highest occupied molecular orbital (HOMO) energy levels and the lowest unoccupied molecular orbital (LUMO) energy levels are synthesized by the present invention on a structural basis using dihydrophenazine as the core to incorporate different functional groups, which have the effect of effectively increasing luminous efficiency of a light emitting structure, while a synthetic route also has improved material synthesis efficiency, which is conducive to the fabrication of organic light emitting diodes with long lifespan and high efficiency.

BRIEF DESCRIPTION OF DRAWINGS

FIG. 1 is a schematic diagram of an organic light emitting diode according to an embodiment of the present invention.

DETAILED DESCRIPTION

In response to urgent needs of high-performance hole transport materials, hole transporting materials using dihydrophenazine as a core with suitable mobilities under highest occupied molecular orbital (HOMO) energy levels and the lowest unoccupied molecular orbital (LUMO) energy levels are synthesized by the present invention on a structural basis using dihydrophenazine as the core to incorporate different functional groups, which have the effect of effectively increasing the luminous efficiency of a light emitting structure, while a synthetic route also has improved material synthesis efficiency, which is conducive to the fabrication of organic light emitting diodes with long lifespan and high efficiency.

In order to achieve the above-mentioned effects, a hole transporting material using dihydrophenazine as a core is provided by the present invention, having the following structural formula (I):

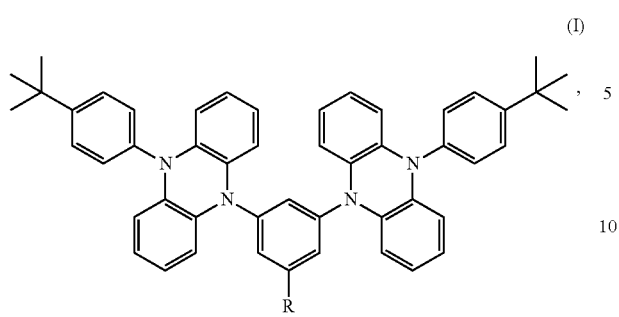
(I)
wherein R is
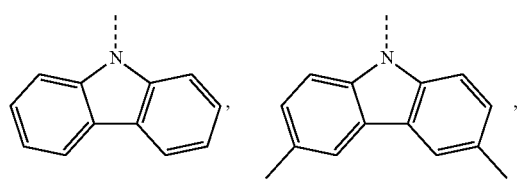
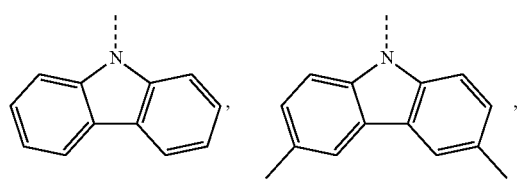
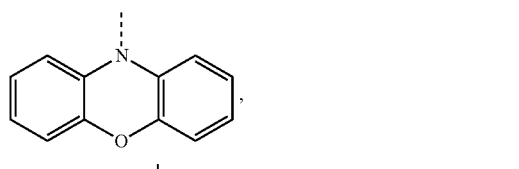
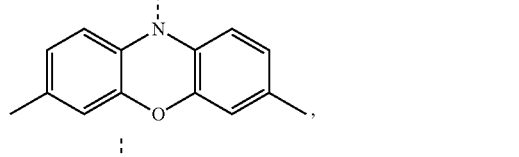
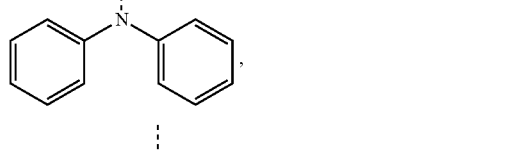
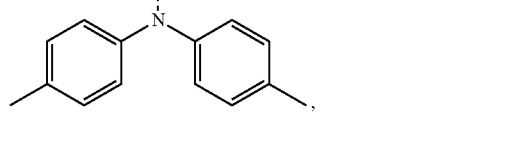
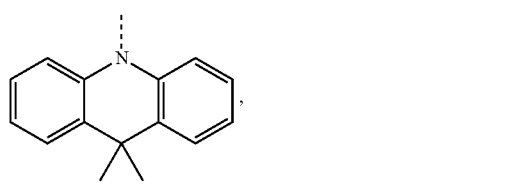
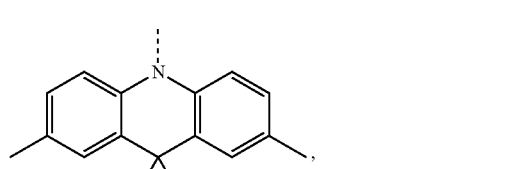
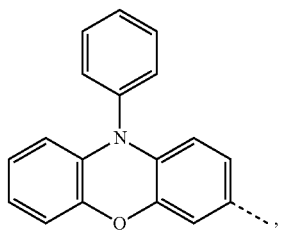
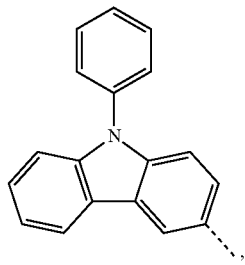
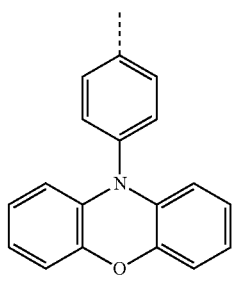
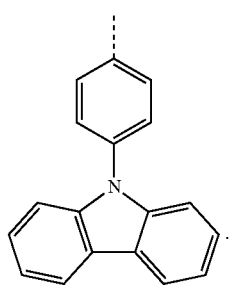
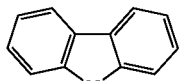
or
In one embodiment of the present invention, the hole transporting material has the following structural formula:
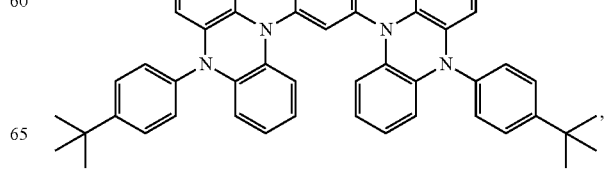

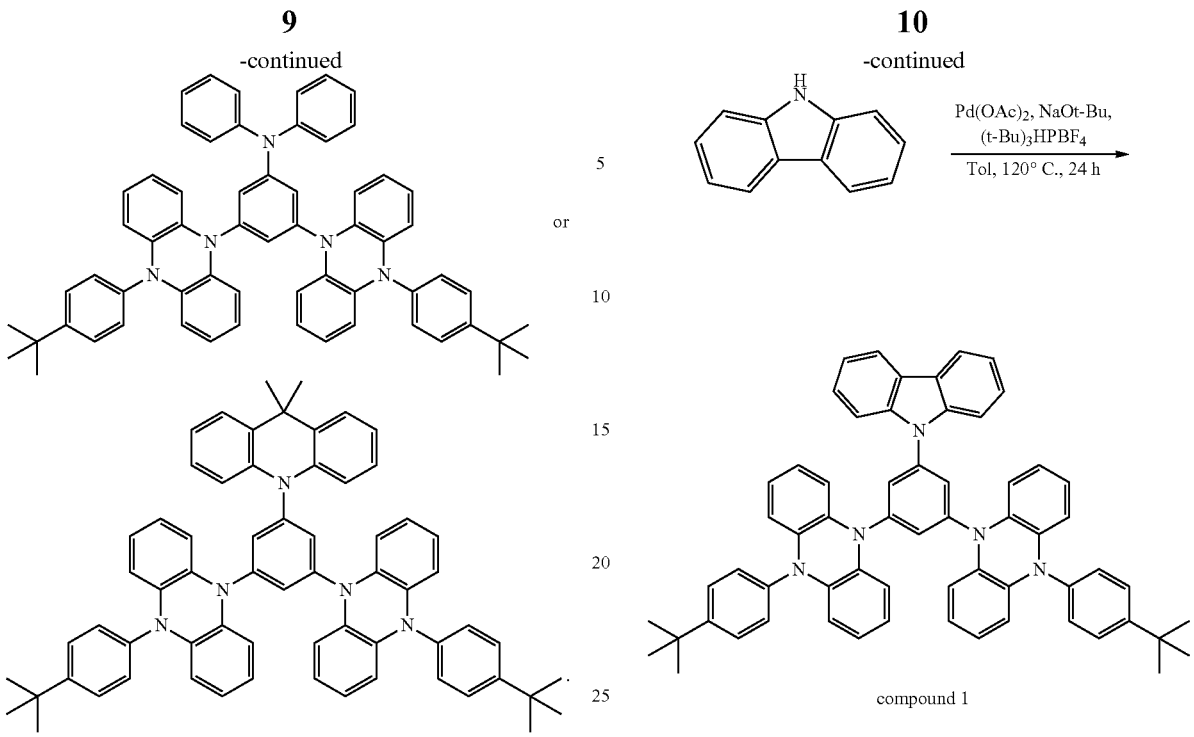

The following further describes the present invention in detail with reference to the embodiments and drawings for purposes of better understanding of the content of the present invention, but the protection scope of the present invention is not limited to these embodiments.

Embodiment 1: fabrication of a hole transporting material using dihydrophenazine as a core having the following structural formula:

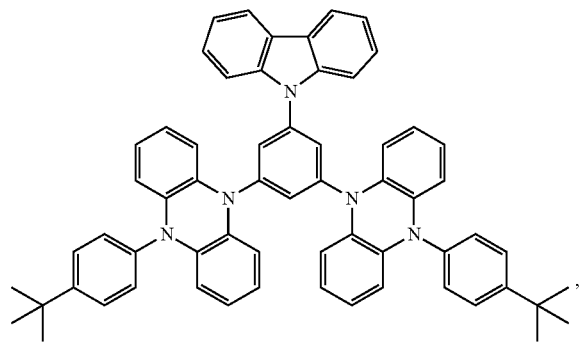 [SMILES: CC(C)(C)c1ccc(N2c3ccccc3N(c3cc(N4c5ccccc5N(c5ccc(C(C)(C)C)cc5)c5ccccc54)cc(-n4c5ccccc5c5ccccc54)c3)c3ccccc32)cc1]

and it is synthesized by the following synthesis route:

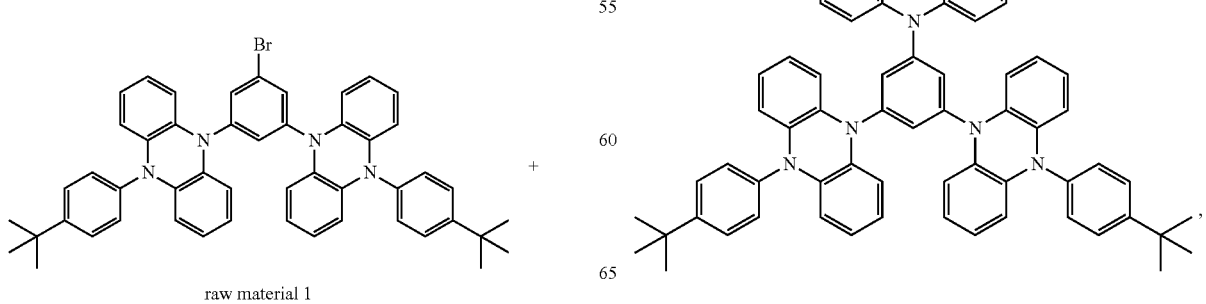

raw material 1

Synthesis of Compound 1

First, 3.90 grams or 5 mmol of raw material 1, 1.00 grams or 6 mmol of carbazole, 0.09 grams or 0.4 mmol of palladium acetate, and 0.34 grams or 1.2 mmol of tri-tert-butylphosphine tetrafluoroborate were added to a 250 mL two-necked flask. The two-necked flask was next placed into a glove box and 0.58 grams or 6 mmol of NaOt-Bu were added. Next, 100 mL of toluene which was previously dehydrated and deoxygenated were injected under an argon atmosphere and were then reacted at 120° C. for 24 hours. A reaction solution was obtained after it was cooled to the room temperature. Subsequently, the reaction solution was introduced into 200 mL of ice water and extracted three times with dichloromethane. The organic phases obtained in each extraction were collected and combined to spin thereof into silica gel, and the silica gel was then subjected to column chromatography (using dichloromethane:n-hexane, v:v, 1:3) for isolation and purification. Finally, 2.1 grams of compound 1 (white powder) were obtained with a yield of 49% and MS (EI) m/z:[M]+: 867.40.

Embodiment 2: fabrication of a hole transporting material having the following structural formula and it is synthesized by the following synthesis route:

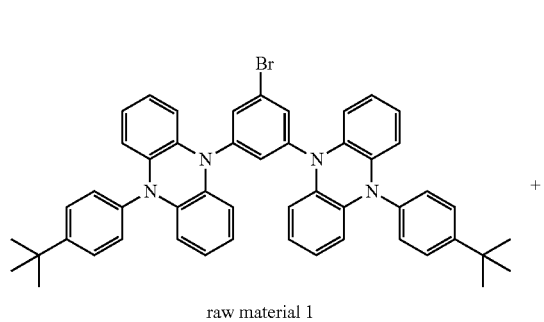

raw material 1

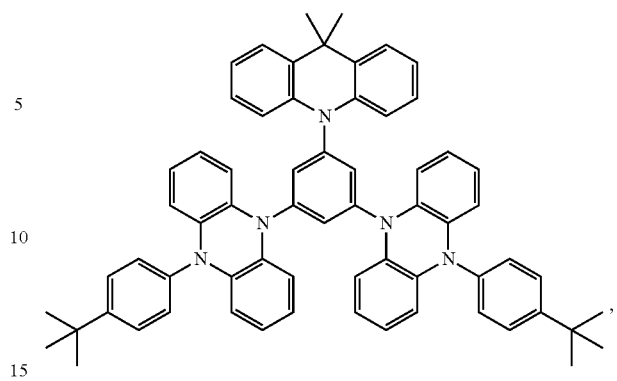

and it is synthesized by the following synthesis route:

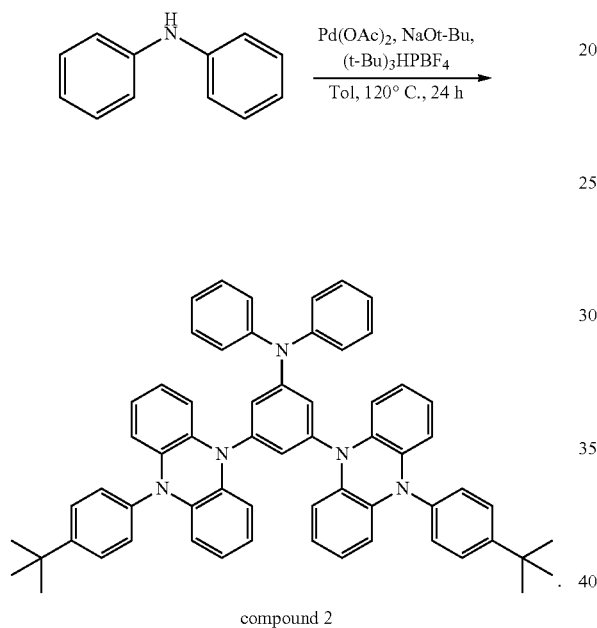

compound 2

Synthesis of Compound 2

First, 3.90 grams or 5 mmol of raw material 1, 1.01 grams or 6 mmol of diphenylamine, 0.09 grams or 0.4 mmol of palladium acetate, and 0.34 grams or 1.2 mmol of tri-tert-butylphosphine tetrafluoroborate were added to a 250 mL two-necked flask. The two-necked flask was next placed into a glove box and 0.58 grams or 6 mmol of NaOt-Bu were added. Next, 100 mL of toluene which was previously dehydrated and deoxygenated were injected under an argon atmosphere and were then reacted at 120° C. for 24 hours. A reaction solution was obtained after it was cooled to the room temperature. Subsequently, the reaction solution was introduced into 200 mL of ice water and extracted three times with dichloromethane. The organic phases obtained in each extraction were collected and combined to spin thereof into silica gel, and the silica gel was then subjected to column chromatography (using dichloromethane:n-hexane, v:v, 1:3) for isolation and purification. Finally, 1.9 grams of compound 2 (white powder) were obtained with a yield of 44% and MS (EI) m/z:[M]+: 869.41.

Embodiment 3: fabrication of a hole transporting material having the following structural formula

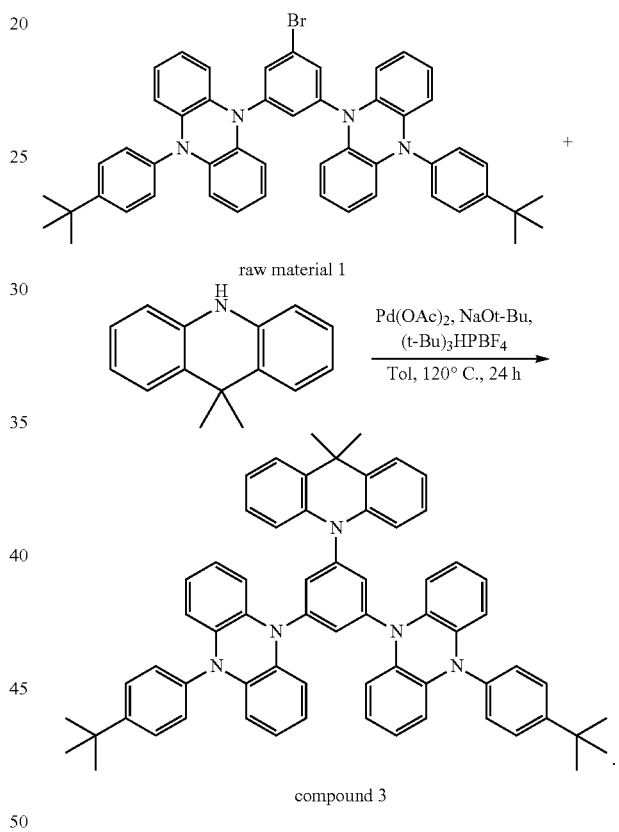

compound 3

Synthesis of Compound 3

First, 3.90 grams or 5 mmol of raw material 1, 1.25 grams or 6 mmol of N,N-dimethylacridine, 0.09 grams or 0.4 mmol of palladium acetate, and 0.34 grams or 1.2 mmol of tri-tert-butylphosphine tetrafluoroborate were added to a 250 mL two-necked flask. The two-necked flask was next placed into a glove box and 0.58 grams or 6 mmol of NaOt-Bu were added. Next, 100 mL of toluene which were previously dehydrated and deoxygenated were injected under an argon atmosphere and were then reacted at 120° C. for 24 hours. A reaction solution was obtained after it was cooled to the room temperature. Subsequently, the reaction solution was introduced into 200 mL of ice water and extracted three times with dichloromethane. The organic phases obtained in each extraction were collected and combined to spin thereof into silica gel, and the silica gel was then subjected to column chromatography (using dichloromethane:n-hexane, v:v, 1:3) for isolation and purification. Finally, 2.1 grams of compound 3 (white powder) were obtained with a yield of 46% and MS (EI) m/z:[M]+: 909.39.

Physical Properties of Compounds 1-3:

The highest occupied molecular orbital (HOMO) energy levels and the lowest unoccupied molecular orbital (LUMO) energy levels of the above compounds 1-3 are shown in the following Table 1:

TABLE 1

|  | HOMO (eV) | LUMO (eV) |
|---|---|---|
| Compound 1 | −5.43 | −2.61 |
| Compound 2 | −5.61 | −2.49 |
| Compound 3 | −5.64 | −2.54 |

The HOMO and LUMO energy levels of the above compounds 1-3 were estimated using the cyclic voltammetry combined with the optical energy gap (Eg) of the molecule in the thin film state according to the following calculation formula:

HOMO=−([Eonset]ox+4.8) eV,

Eg=LUMO−HOMO, wherein [Eonset]ox refers to the redox starting potential value of ferrocene under testing.

Embodiments 4-6

Fabrication of an organic light emitting diode:

Referring to FIG. 1, an organic light emitting diode of the present invention comprises a conductive anode glass layer S, a semi-transparent cathode layer 8 and a light-coupling output layer 9, and a light emitting structure formed between the conductive anode glass layer S and the semi-transparent cathode layer 8. Specifically, the light emitting structure comprises a hole injecting layer 1, a hole transporting layer 2, an electron blocking layer 3, a light emitting layer 4, a hole blocking layer 5, an electron transporting layer 6, and an electron injection layer 7, which are sequentially formed on the conductive anode glass layer S. Specifically, the conductive anode glass layer S was formed by plating a glass substrate with a total reflection substrate layer made of a conductive reflective indium tin oxide (ITO)/silver (Ag)/indium tin oxide (ITO). The hole injection layer 1 was composed of 2,3,6,7,10,11-hexacyano-1,4,5,8,9,12-hexaazabenzophenanthrene (HATCN). The hole transporting layer 2 was composed of a hole transporting material using dihydrophenazine as a core according to the present invention, which is, for example, compounds 1-3. The electron blocking layer 3 was composed of 4-[1-[4-[bis (4-methylphenyl)amino]phenyl]cyclohexyl]-N-(3-methylphenyl)-N-(4-methyl Phenyl) aniline (TAPC). The light emitting layer 4 was composed of bis [2-((oxo) diphenylphosphino) phenyl]ether (DPEPO) and Bis[4-(9,9-dimethyl-9,10-dihydroacridine)phenyl]sulfone (DMAC-DPS). The hole blocking layer 5 was composed of 3,3'-[5'-[3-(3-pyridyl) phenyl][1,1':3',1''-terphenyl]-3,3''-diyl]dipyridine (TMPyPb). The electron transport layer 6 was composed of 1,3,5-tris[3-(3-pyridyl)phenyl]benzene (TmPyPB) and lithium octahydroxyquinoline (LiQ). The electron injection layer 7 was composed of lithium fluoride (LiF). The semi-transparent cathode layer 8 was composed of magnesium and silver. The light-coupling output layer 9 was composed of 4,4',4''-tris (carbazole-9-yl) triphenylamine (TCTA). The hole injection layer 1, the hole transport layer 2, the electron blocking layer 3, the light emitting layer 4, the hole blocking layer 5, the electron transport layer 6, and the electron injection layer 7 constitute the light emitting structure of the organic light emitting diode of the present invention. The organic light emitting diode can be completed according to a method known in the technical field of the present invention, for example, the method disclosed in the reference "Adv. Mater. 2003, 15, 277". The specific method is described as follows: under high vacuum conditions, the aforementioned materials containing the hole transporting material (compounds 1-3) of the present invention were sequentially formed on a conductive glass by evaporation to complete the process. Here, the compounds 1-3 of the present invention were used to prepare the organic light emitting diodes I-III of Examples 4-6. The structure of the organic light emitting diode I-III from the conductive glass anode layer S to the light-coupling output layer 9 are provided as follows:

Organic light emitting diode (OLED) I: ITO/Ag/ITO (15 nm/140 nm/15 nm)/HATCN (100 nm)/Compound 1 (130 nm)/TAPC (5 nm)/DMAC-DPS (38 nm: 4 nm)/TMPyPb (15 nm)/TmPyPB:LiQ (15 nm: 15 nm)/LiF (1 nm)/Mg:Ag (1 nm: 10 nm)/TCTA (100 nm).

OLED II: ITO/Ag/ITO (15 nm/140 nm/15 nm)/HATCN (100 nm)/Compound 2 (130 nm)/TAPC (5 nm)/DMAC-DPS (38 nm: 4 nm)/TMPyPb (15 nm)/TmPyPB:LiQ (15 nm: 15 nm)/LiF (1 nm)/Mg:Ag (1 nm: 10 nm)/TCTA (100 nm).

OLED III: ITO/Ag/ITO (15 nm/140 nm/15 nm)/HATCN (100 nm)/Compound 3 (130 nm)/TAPC (5 nm)/DMAC-DPS (38 nm: 4 nm)/TMPyPb (15 nm)/TmPyPB:LiQ (15 nm: 15 nm)/LiF (1 nm)/Mg:Ag (1 nm: 10 nm)/TCTA (100 nm).

Data of performance the organic light emitting diodes I-III of Examples 4-6 are shown in the following Table 2. Current, brightness and voltage of the organic light emitting diodes were measured by a Keithley source measurement system (Keithley 2400 Source-meter, Keithley 2000 Current-meter) with a calibrated silicon photodiode. The electroluminescence spectrum of the organic light emitting diodes were measured by SPEX CCD3000 spectrometer of the French company JY. All measurements were made and done at room temperature.

TABLE 2

| OLED | Hole transporting material | Max current efficiency (cd/A) | chromaticity coordinate (CIEx, CIEy) | Max external quantum efficiency (%) |
|---|---|---|---|---|
| I | Compound 1 | 5.6 | (0.12, 0.045) | 11.3% |
| II | Compound 2 | 5.8 | (0.12, 0.045) | 12.1% |
| III | Compound 3 | 6.1 | (0.12, 0.045) | 12.9% |

In the hole transporting material using dihydrophenazine as the core provided by the present invention, the hole transporting materials using dihydrophenazine as a core with suitable mobilities under highest occupied molecular orbital (HOMO) energy levels and the lowest unoccupied molecular orbital (LUMO) energy levels are synthesized on a structural basis using dihydrophenazine as the core to incorporate different functional groups, which have the effect of effectively increasing the luminous efficiency of a light emitting structure. In addition, a synthetic route of the hole transporting materials using dihydrophenazine as a core of the present invention is also provided with improved material synthesis efficiency. At last, an organic light emitting diode adopting the hole transporting material using dihydrophenazine as a core in the embodiment of the present invention as a light emitting structure has high light emitting efficiency, thereby facilitating the production of a long-life, high efficiency organic light emitting diode, which can be applied and used in various display devices and electronic devices.

While the present disclosure has been described with the aforementioned preferred embodiments, it is preferable that the above embodiments should not be construed as limiting of the present disclosure. Anyone having ordinary skill in the art can make a variety of modifications and variations without departing from the spirit and scope of the present disclosure as defined by the following claims.

What is claimed is:

1. A hole transporting material using dihydrophenazine as a core, wherein the hole transporting material has a following structural formula (I):

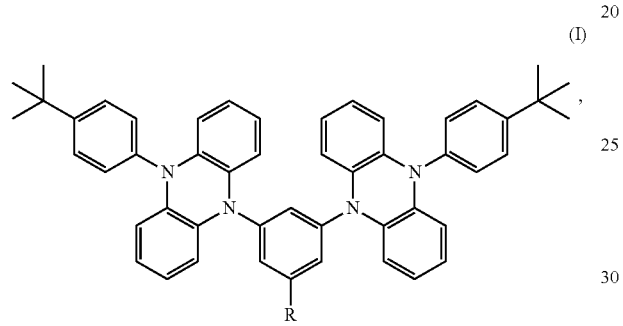

wherein R is

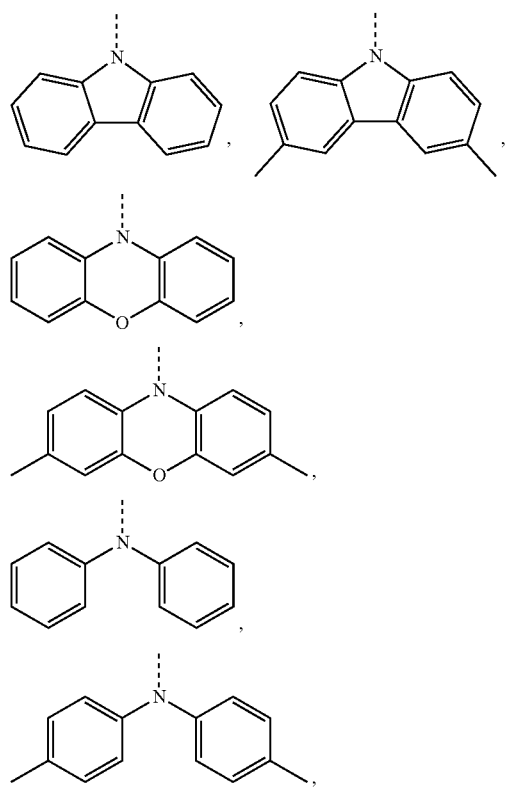

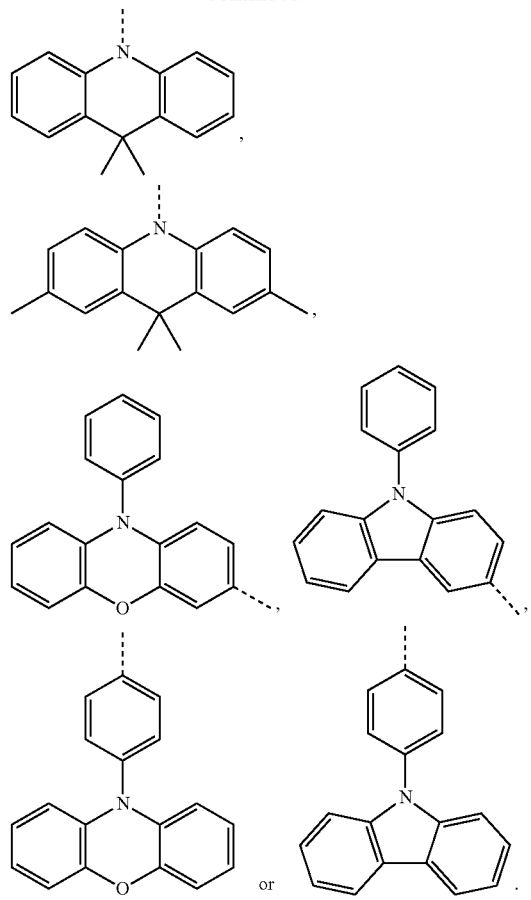

2. The hole transporting material according to claim 1, wherein the hole transporting material has the following structural formula:

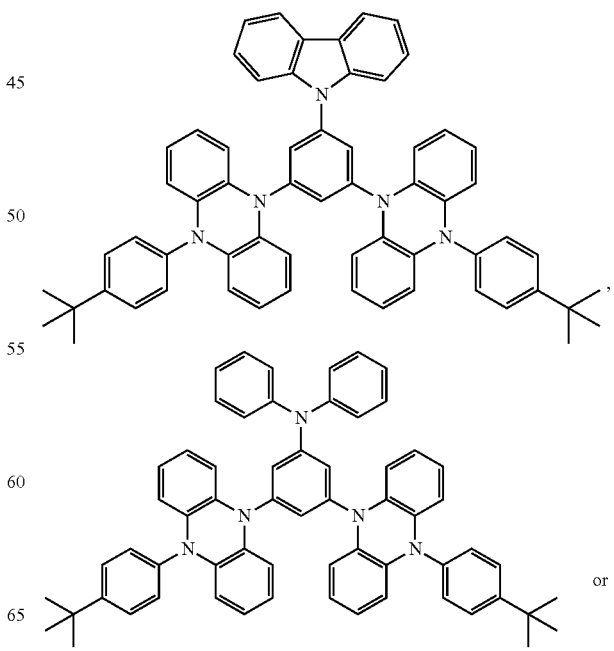

-continued

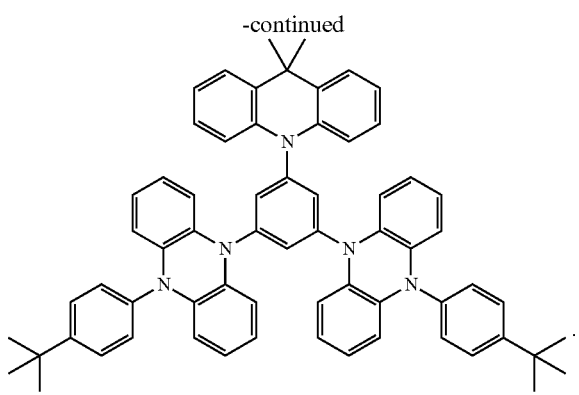

3. The hole transporting material according to claim 2, wherein the hole transporting material has the following structural formula:

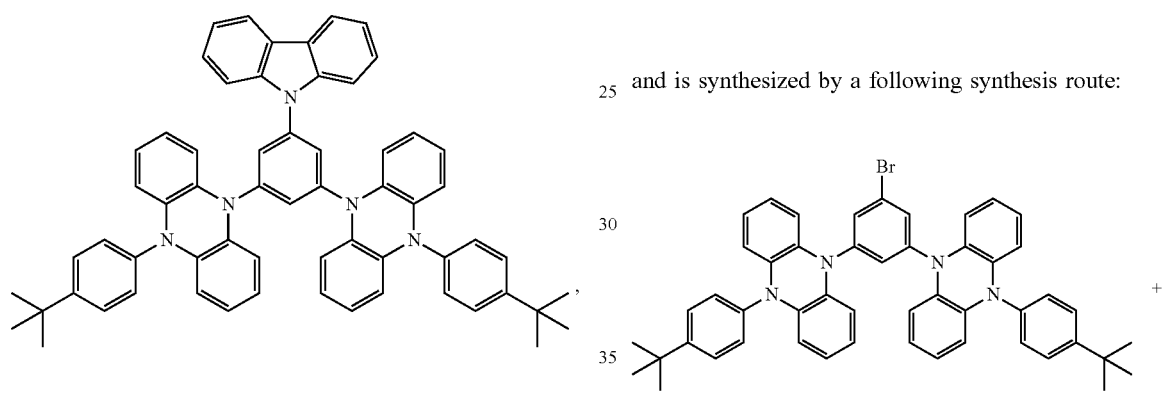

and is synthesized by a following synthesis route:

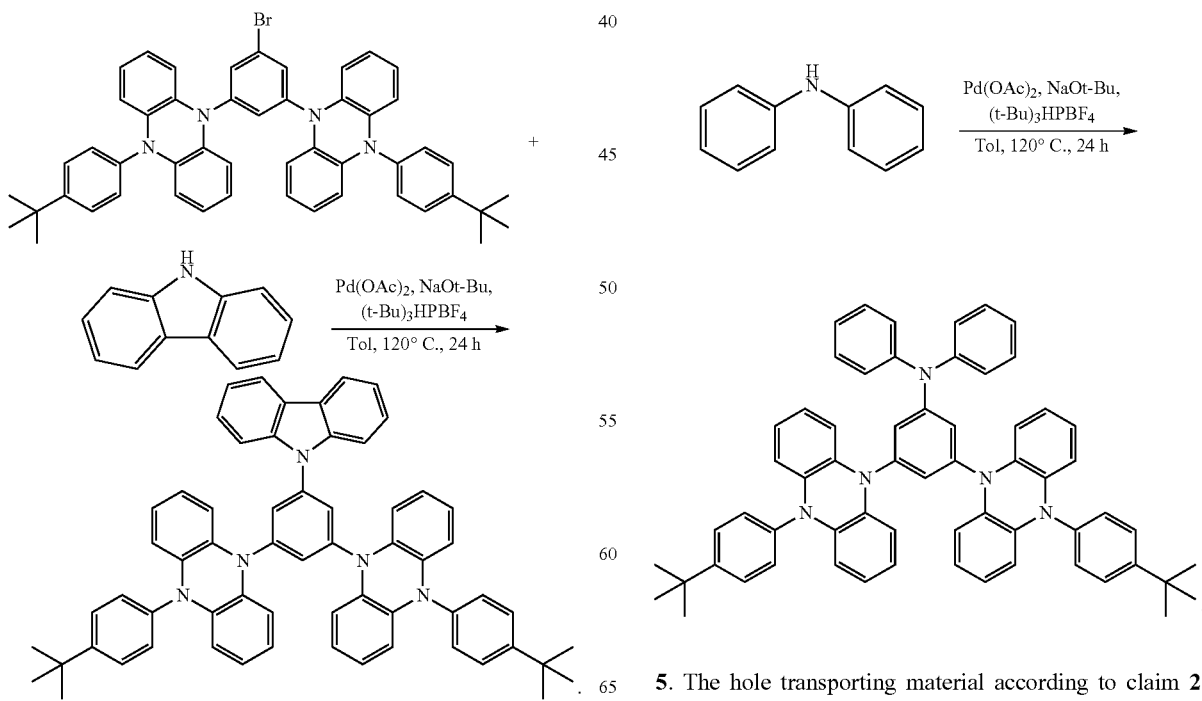

4. The hole transporting material according to claim 2, wherein the hole transporting material has the following structural formula:

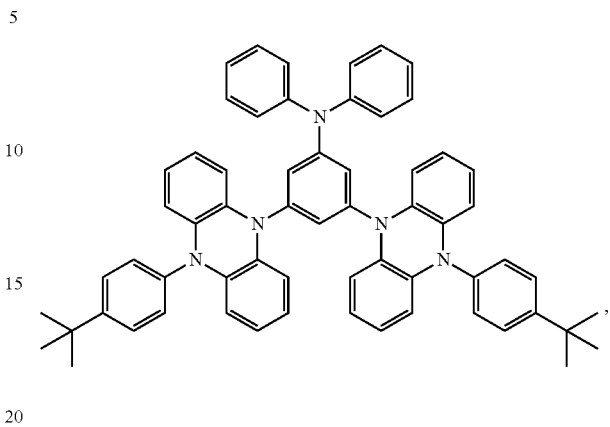

and is synthesized by a following synthesis route:

5. The hole transporting material according to claim 2, wherein the hole transporting material has the following structural formula:

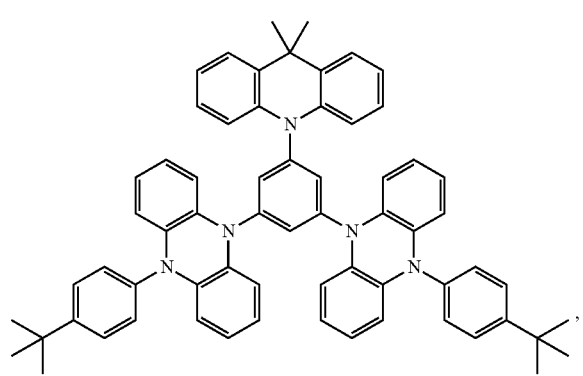 [SMILES: CC(C)(C)c1ccc(N2c3ccccc3N(c3cc(N4c5ccccc5N(c5ccc(C(C)(C)C)cc5)c5ccccc54)cc(N4c5ccccc5C(C)(C)c5ccccc54)c3)c3ccccc32)cc1]
and is synthesized by a following synthesis route:
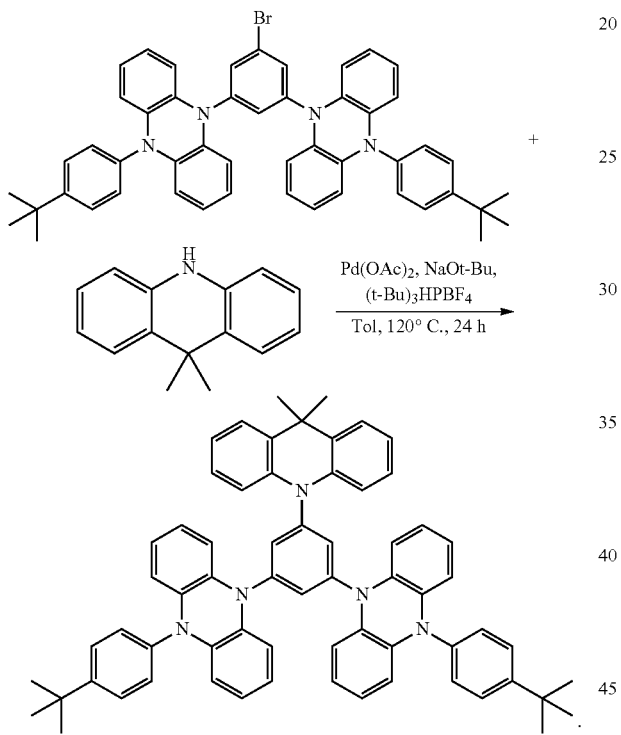
6. An organic light emitting diode, wherein a material of a hole transport layer in the organic light emitting diode is a hole transporting material using dihydrophenazine as a core and has a following structural formula (I):
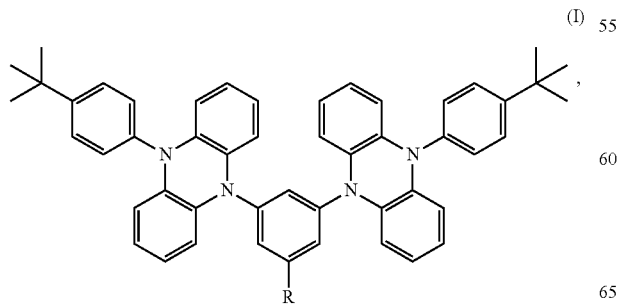
(I)
wherein R is
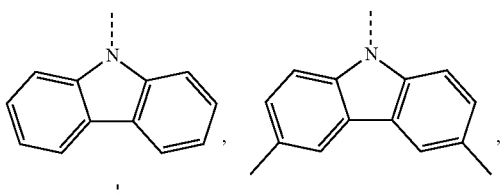
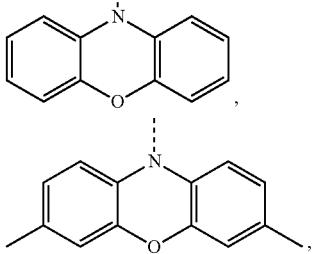
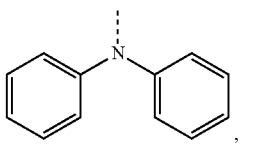
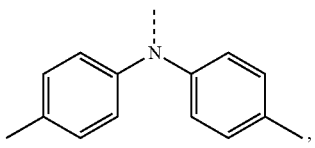
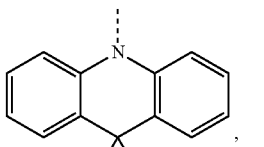
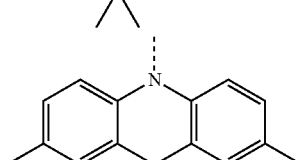
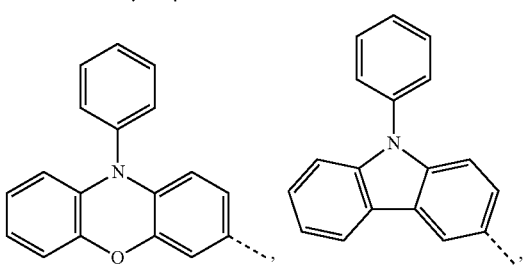
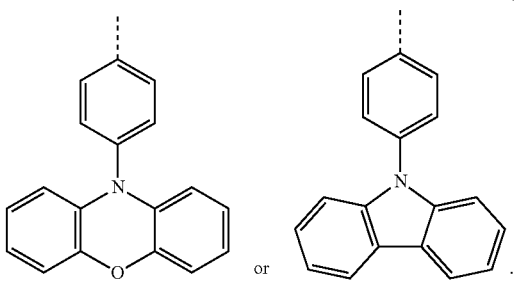
or .

7. The organic light emitting diode according to claim 6, wherein the hole transporting material has the following structural formula:

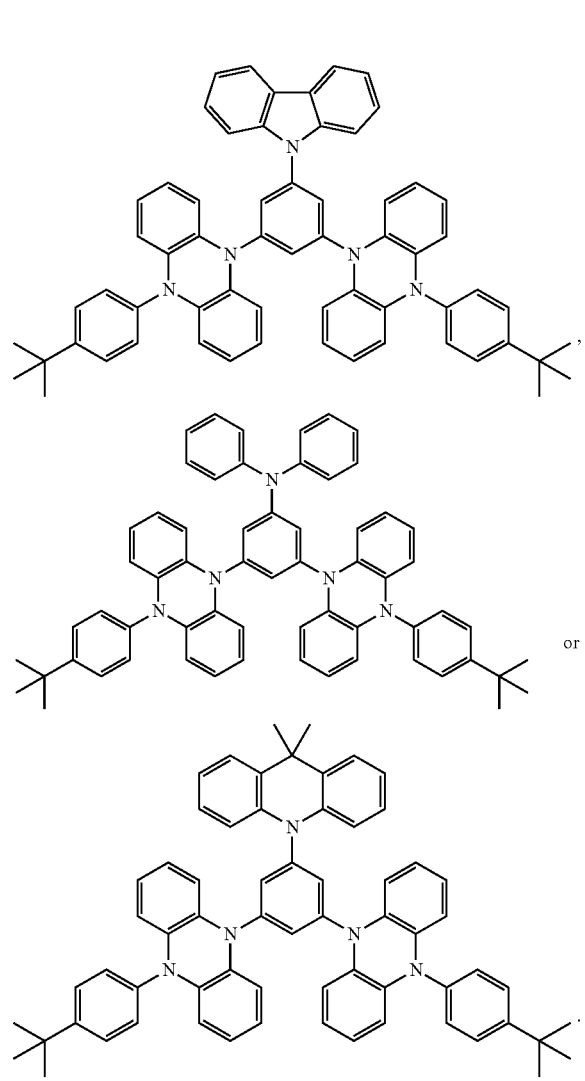

or

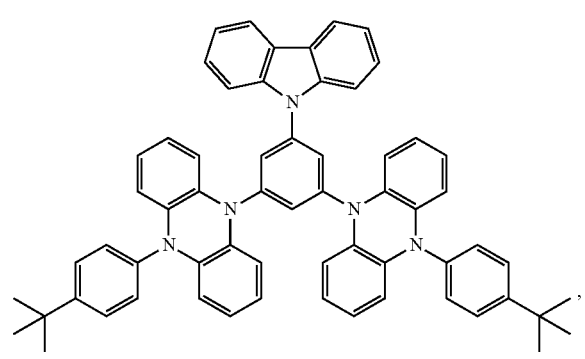 [SMILES: CC(C)(C)c1ccc(N2c3ccccc3N(c3cc(N4c5ccccc5N(c5ccc(C(C)(C)C)cc5)c5ccccc54)cc(-n4c5ccccc5c5ccccc54)c3)c3ccccc32)cc1]

8. The organic light emitting diode according to claim 7, wherein the hole transporting material has the following structural formula:

and is synthesized by a following synthesis route:

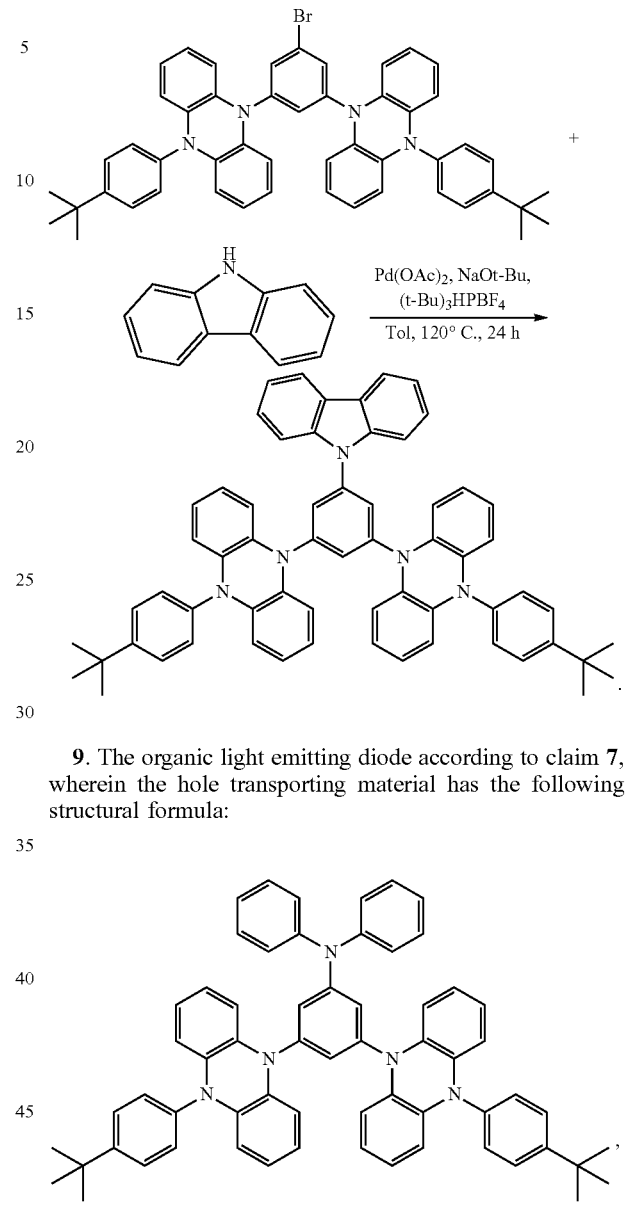

9. The organic light emitting diode according to claim 7, wherein the hole transporting material has the following structural formula:

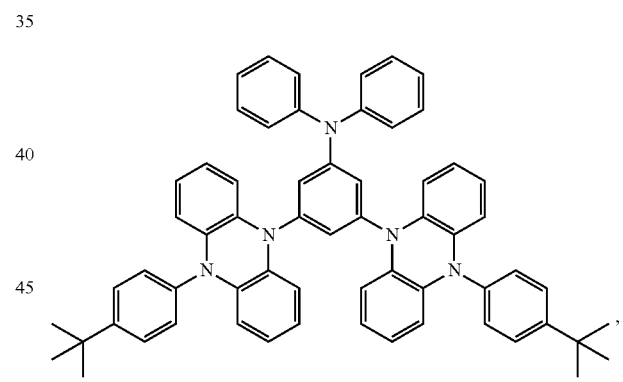

and is synthesized by a following synthesis route:

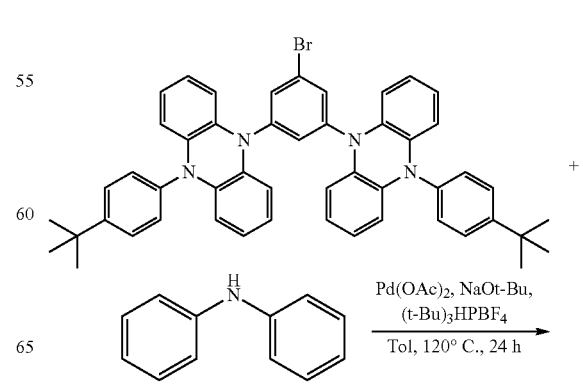

-continued

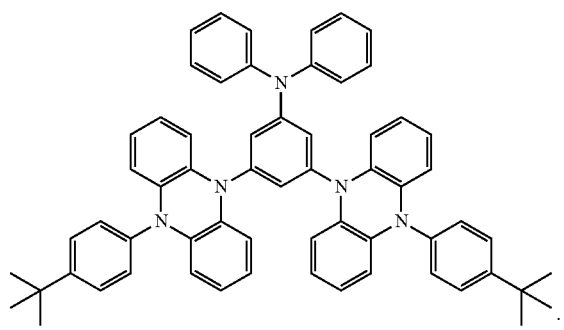 [SMILES: CC(C)(C)c1ccc(N2c3ccccc3N(c3cc(N(c4ccccc4)c4ccccc4)cc(N4c5ccccc5N(c5ccc(C(C)(C)C)cc5)c5ccccc54)c3)c3ccccc32)cc1]

and is synthesized by a following synthesis route:

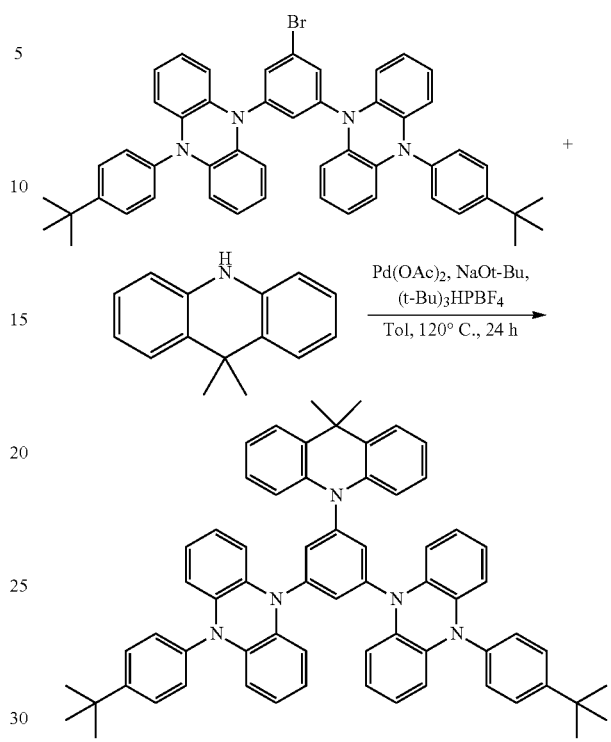

10. The organic light emitting diode according to claim 7, wherein the hole transporting material has the following structural formula:

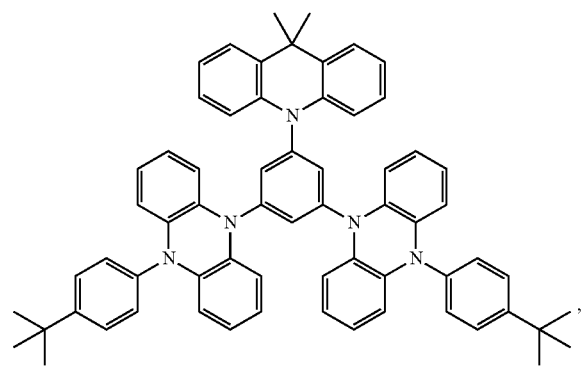 [SMILES: CC(C)(C)c1ccc(N2c3ccccc3N(c3cc(N4c5ccccc5N(c5ccc(C(C)(C)C)cc5)c5ccccc54)cc(N4c5ccccc5C(C)(C)c5ccccc54)c3)c3ccccc32)cc1]

11. The organic light emitting diode according to claim 6, wherein the organic light emitting diode further comprises an anode, a cathode, and a light emitting structure located between the anode and the cathode, wherein the light emitting structure comprises the hole transporting layer according to claim 6.

12. The organic light emitting diode according to claim 11, wherein the light emitting structure comprises a hole injecting layer, the hole transporting layer, an electron blocking layer, a light emitting layer, a hole blocking layer, an electron transporting layer, and an electron injecting layer, which are sequentially formed.

* * * * *